United States Patent [19]

Basset et al.

[11] Patent Number: 4,720,594

[45] Date of Patent: Jan. 19, 1988

[54] PROCESS FOR THE PREPARATION OF AROMATIC ALDEHYDES

[75] Inventors: Jean-Marie Basset, Villeurbanne; Robert Mutin, Meyzieu, both of France

[73] Assignee: Rhone-Poulenc Specialites Chimiques, France

[21] Appl. No.: 873,964

[22] Filed: Jun. 13, 1986

[30] Foreign Application Priority Data

Jun. 21, 1985 [FR] France .................................. 85 09676

[51] Int. Cl.$^4$ ............................................ C07C 45/49
[52] U.S. Cl. .................................................. 568/428
[58] Field of Search ........................................ 568/428

[56] References Cited

U.S. PATENT DOCUMENTS 3,960,932 6/1976 Heck .
4,536,344 8/1985 Fiedler et al. .................. 568/428 X
4,605,749 8/1986 Buchman et al. ............... 568/428 X

FOREIGN PATENT DOCUMENTS 0109606 8/1983 European Pat. Off. .
3242582 A1 5/1984 Fed. Rep. of Germany .

OTHER PUBLICATIONS

Schoenberg et al., J. Am. Chem. Soc. 96, 7761–7764 (1974).
Hajime Yoshida et al., Kinetics on the Formylation of Iodobenzene Catalyzed by Palladium(II) Chloride in a Pyridine Solution, Bulletin of the Chemical Society of Japan, vol. 49 (6), 1681–1685 (1976).

Primary Examiner—Werren B. Lone
Attorney, Agent, or Firm—Finnegan, Henderson, Farabow, Garrett & Dunner

[57] ABSTRACT

Process for the preparation of aromatic aldehydes by hydrocarbonylation of chloro- or bromoaromatic compounds. In the presence of an acceptor for an oxygen-free acid, a palladium/phosphine complex and, if appropriate, a phosphine, a mixture of carbon monoxide and hydrogen is reacted with chloro- or bromoarenetricarbonylchromiums.

18 Claims, No Drawings

PROCESS FOR THE PREPARATION OF AROMATIC ALDEHYDES

The present invention relates to a process for the preparation of aromatic aldehydes by hydrocarbonylation of halogenated aromatic compounds in the presence of a noble metal complex.

In view of the plentifulness and the low cost of carbon monoxide, industry is interested in the production of aromatic aldehydes by hydrocarbonylation of aromatic halides. To this end, A. Schoenberg and R. F. Heck, J. Am. Chem. Soc. 96 7761–7764 (1974) have proposed reacting a mixture of carbon monoxide and hydrogen with aromatic iodides and bromides in the presence of an amine acting as an acceptor for an oxygen-free acid and a dihalodiphosphinopalladium as catalyst (cf. also U.S. Pat. No. 3,960,932). German Patent Application No. 3,242,582 offered an improvement to this process, consisting of operating in the presence of a phosphine or a free phosphite to increase the reaction efficiency.

Despite industry interest, from an industrial standpoint a major disadvantage of these processes is that they involve the use of aryl bromides or iodides to produce satisfactory yields of aromatic aldehydes. It has been found that aryl chlorides lead to poor yields of aldehydes because of the low reactivity of the bond between chlorine and an aromatic ring carbon, even under severe pressure and temperature conditions (cf. H. Yoshiba et al, Bull. Chem. Soc. Jap. 49 (1976)). As a result, the problem of the hydrocarbonylation of aryl chlorides, which are less costly than the bromides or iodides, remains to be solved.

The aim of the present invention is to provide a solution to the problem posed by the activation of the bond between chlorine and an aromatic ring carbon, so as to make carbonylation of aromatic chlorides possible. Furthermore, the presence of electrondonating substituents on the aromatic residue of aromatic bromides slightly reduces the reactivity of the bond between bromine and an aromatic ring carbon, which is reflected in lower aldehyde yields. Consequently, another subject of the present invention is a process of hydrocarbonylation of aromatic bromides containing electron-donating substituents.

More particularly, the present invention relates to a process for the preparation of an aromatic aldehyde by hydrocarbonylation of a chloro- or bromoaromatic compound comprising the step of reacting a mixture of carbon monoxide and hydrogen with a chloro- or bromoarenecarbonylchromium in the presence of an acceptor for an oxygen-free acid, a source of palladium/phosphine complex catalyst and, if appropriate, a free phosphine.

It has unexpectedly been found that the presence of a carbonylchromium residue —Cr(CO)$_3$ on the aromatic nucleus of aromatic chlorides and of aromatic bromides containing electrondonating substituents activates the halogen-carbon bond to a marked degree and makes it possible to improve the yields of aromatic aldehydes.

Arenetricarbonylchromium compounds are known products which may be obtained readily by various synthetic routes (cf. G. Wilkinson et al., Comprehensive Organometallic Chemistry, vol. 3 pages, 1001–1021, published by Pergamon Press). A preferred route of access to arenetricarbonylchromiums consists of reacting an aromatic compound with hexacarbonylchromium in various organic solvents such as hydrocarbons and/or ethers, or in an excess of the original aromatic compound. This method is most particularly suitable for the synthesis of arenetricarbonylchromiums containing electron-donating substituents.

Still more particularly, the subject of the present invention relates to a process for the preparation of an aromatic aldehyde preferably corresponding to the formula (I):

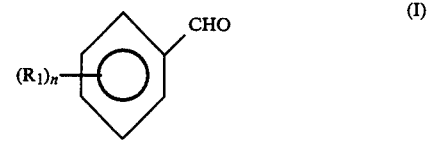

by hydrocarbonylation of a haloarenetricarbonylchromium compound preferably of the formula (II):

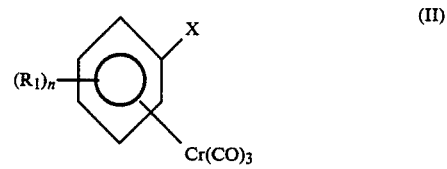

wherein

R$_1$ denotes an alkyl radical containing from 1 to 20 carbon atoms, a cycloalkyl radical, an arylalkyl radical, an alkoxy radical containing from 1 to 20 carbon atoms, a fluorine atom, a mono- or polyhalogenated alkyl residue, a formyl group, a carbonyloxyalkyl group, a tertiary amino group, a hydroxyl group, an acyl residue, or an acylamine residue;

n denotes an integer from 1 to 3, preferably from 1 to 2; and

X denotes a chlorine or bromine atom.

Illustrative examples of radicals R$_1$ which may be employed include methyl, ethyl, n-propyl, isopropyl, n-butyl, isobutyl, sec-butyl, n-pentyl, 2-ethylhexyl, dodecyl, octadecyl, cyclohexyl, methylcyclohexyl, benzyl and 2-phenylethyl radicals, alkoxy radicals such as methoxy, ethoxy, n-propoxy, isopropoxy, n-butoxy, 2-ethylhexyloxy, dodecyloxy or hexadecyloxy radicals, haloalkyl radicals such as trifluoromethyl, difluorochloromethyl or perfluoroethyl, carbonyloxyalkyl groups in which the alkyl residue contains from 1 to 4 carbon atoms, such as carbonyloxymethyl, carbonyloxyethyl or carbonyloxyisopropyl groups, tertiary amino residues of the formula:

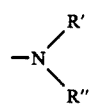

wherein R' and R", which may be identical or different, denote alkyl radicals containing from 1 to 20 carbon atoms, such as those mentioned in the case of R$_1$, arylalkyl radicals, phenyl radicals, acyl and acylamino residues of the formulae:

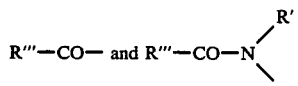

wherein R'''denotes alkyl, cycloalkyl or arylalkyl radicals) such as those mentioned in the case of $R_1$, and aryl radicals (phenyl, toluoyl, naphthyl). Illustrative acyl and acylamino radicals include acetyl, propionyl, benzoyl, methylbenzoyl, acetylmethylamino and ethylbenzoylamino radicals. When X denotes a bromine atom, $R_1$ preferably denotes an electron-donating residue.

$R_1$ preferably denotes a lower alkyl radical, such as an alkyl radical containing from 1 to 4 carbon atoms.

Illustrative haloarenetricarbonylchromiums include:
chlorobenzenetricarbonylchromium,
chlorotoluenetricarbonylchromium,
bromotoluenetricarbonylchromium,
fluorochlorobenzenetricarbonylchromium,
1-methyl-4-fluoro-2-chlorobenzenetricarbonylchromium,
1-chloro-4-trifluoromethylbenzenetricarbonylchromium,
1-chloro-4-tert-butylbenzenetricarbonylchromium,
1-chloro-4-methoxybenzenetricarbonylchromium,
1-bromo-4-methoxybenzenetricarbonylchromium,
1-chloro-2-methoxybenzenetricarbonylchromium,
1-chloro-4-hydroxybenzenetricarbonylchromium,
1-chloro-2-hydroxybenzenetricarbonylchromium,
1-bromo-4-diethylaminobenzenetricarbonylchromium,
1-chloro-3-methoxycarbonylbenzenetricarbonylchromium,
2-bromo-3-methoxycarbonylbenzenetricarbonylchromium, and
1-chloro-4-acetylbenzenetricarbonylchromium.

The process of the present invention is particularly highly suitable for the preparation of aldehydes such as benzaldehyde, p-hydroxybenzaldehyde, p-methoxybenzaldehyde, p-tolualdehyde, p-trifluoromethylbenzaldehyde and p-trifluoromethoxybenzaldehyde.

To make use of the process according to the invention it is possible to employ any acceptor for an oxygen-free acid which is soluble in the reaction medium or miscible with the components of the reaction medium and which does not liberate water during the reaction with the oxygen-free acid which is formed. It is possible to use alkaline-earth metal oxides (CaO), alkali metal or alkaline-earth metal carbonates and bicarbonates (sodium carbonate and bicarbonate), alkali metal or alkaline-earth metal carboxylates derived from weak carboxylic acids (carboxylic acids which have a pK higher than 4 in water at 25° C.), such as sodium or potassium acetates, propionates, butyrates, isobutyrates, benzoates or phenylacetates, tertiary amines and tertiary nitrogenous heterocyclic bases such as trimethylamine, triethylamine, methyltriethylamine, pyridine, picolines and N-alkylpiperidines (for example N-methyl- or N-ethylpiperidines). Tertiary amines and tertiary heterocyclic nitrogenous bases constitute a preferred category of acceptors for oxygen-free acids.

The quantity of an acceptor for an oxygen-free acid is preferably at least close to the stoichiometric quantity required for the neutralization of the oxygen-free acid formed during the reaction, that is to say close to at least 1 mole per mole of chloro- or bromoarenetricarbonylchromium. At least 1.1 mole of acceptor of oxygen-free acid is preferably employed per mole of the chloro- or bromoarenetricarbonylchromium. There is no critical upper limit to the quantity of the acceptor for oxygen-free acid, and in the case of tertiary nitrogenous bases, the latter may form the reaction medium. In the case of other acceptors for oxygen-free acids it is unnecessary, in general, to make use of more than 1.5 moles of acceptor per mole of the chloro- or bromoarenetricarbonylchromium; a quantity in the range of from 1 to 1.25 is, as a general rule, satisfactory.

The palladium-phosphine complexes used as catalysts in the process of the present invention are those usually employed in the reactions of hydrocarbonylation of aromatic halides (cf. A. Schoenberg et al, loc. cit., H. Yoshida et al, loc. cit.; U.S. Pat. No. 3,960,932 and German Application No. 3,242,582). It is possible, therefore, to make use of zerovalent palladium complexes or of divalent palladium complexes equally well; the latter are generally preferred because of their stability in air, which makes them easier to handle. More specifically, use may be made of palladium complexes of the general formulae:

 (IV)

 (V)

 (VI)

 (VII)

wherein
$R_2$ denotes a saturated aliphatic or alicyclic or aromatic hydrocarbon radical containing from 1 to 20 carbon atoms;
Z denotes a halogen atom or an acyloxy residue of the formula $R_3$-COO- in which $R_3$ denotes an alkyl, cycloalkyl or arylalkyl radical containing from 1 to 20 carbon atoms, such as those mentioned above for $R_1$ or aryl; and
m is 3 or 4.

In formulae (IV) through (VII) the radicals $R_2$, which may be identical or different, more particularly denote methyl, ethyl, propyl, isopropyl, n-butyl, sec-butyl, n-octyl, cyclohexyl, methylcyclohexyl, phenyl, toluyl, ethylphenyl, xylyl, naphthyl, benzyl and 2-phenylethyl radicals. At least one of the radicals $R_2$ preferably denotes an electron-donating radical and, still more preferably, an aryl radical.

Z preferably denotes a chlorine or bromine atom or a lower saturated aliphatic acyloxy (acetoxy, propionyloxy or butyryloxy) radical or an aromatic acyloxy (benzoyloxy or toluyloxy) residue.

Exemplary palladium/phosphine complexes are: tris(methyldiphenylphosphino)monocarbonylpalladium, tris(triphenylphosphino)monocarbonylpalladium, tris(ethylditolylphosphino)monocarbonylpalladium, tris(ethylditolylphosphino)palladium, tetrakis(tritolylphosphino)palladium, dichlorobis(triphenylphosphino)palladium, dichlorobis(tritolylphosphino)palladium, and diisopropionyloxybis(triphenylphosphino)palladium. Preferably, dihalobis(triarylphosphino)palladiums, diacyloxybis(triarylphosphino)palladiums, dichloro- or diacetoxybis(phosphino)palladium complexes in which the phosphine is tris(hydroxysulphonylphenyl)phosphine, or the sodium or potassium salts of the complexes are employed. Preferably, dihalobis(triarylphosphino)palladium and diacyloxybis(triarylphosphino)palladium are employed.

The process of the present invention is conducted in the presence of a solvent for the various compounds taking part in the reaction, which is inert under the reaction conditions and which is practically anhydrous. As already indicated, a first group of solvents which can be used for this purpose consists of the tertiary nitrogenous bases used as an acceptor for an oxygen-free acid. It is also possible to use other organic compounds such as saturated aliphatic hydrocarbons (for example hexane), saturated alicyclic hydrocarbons (cyclohexane or methylcyclohexane), aromatic hydrocarbons (benzene, toluene, xylenes or ethylbenzene), halogenated aromatic hydrocarbons (chlorobenzene or chlorotoluenes), aliphatic ethers, cyclic ethers (tetrahydrofuran), aromatic ethers (anisole, chloroanisoles or bromanisoles), lactams (N-methylpyrrolidone), ethers of mono- or dicarboxylic acids (methyl adipate or methyl terephthalate) and polyol ethers (ethylene glycol dimethyl ether or diethylene glycol dimethyl ether).

Generally, use is made of organic compounds which are as weakly electron-donating in their nature as possible. It has been found to be especially advantageous to use as a solvent or cosolvent the haloaromatic derivative from which the haloarenetricarbonylchromium was derived, when it is liquid under normal pressure and temperature conditions. The latter is prepared by reacting hexacarbonylchromium with an excess of haloaromatic compound; the haloarenetricarbonylchromium solution thus obtained is used directly in the hydrocarbonylation reaction.

The concentration of the reactants in the reaction medium is not critical and may vary within wide limits.

The quantity of palladium catalyst, expressed as the number of gram-atoms of palladium per mole of haloarenetricarbonylchromium, may vary within wide limits. In general it may lie in a range from $1 \times 10^{-5}$ to 0.5 gram-atom of palladium per mole of haloarenetricarbonylchromiums; quantities ranging from $1 \times 10^{-4}$ to $1 \times 10^{-1}$ gram-atom of palladium per mole of haloarenetricarbonylchromiums are particularly suitable.

The hydrocarbonylation of haloarenetricarbonylchromiums is preferably carried out in the presence of a free phosphine, which is advantageously the same as that bound to the palladium in the catalyst. Generally, it is possible to use the phosphines mentioned in German Application No. 3,242,582, specifically incorporated by reference herein. The quantity of phosphine, expressed in gram atom of phosphorus per g atom of palladium, may vary within wide limits as a function of the palladium concentration in the medium; the free phosphine/palladium ratio is preferably inversely proportional to the palladium concentration in the medium. As a general rule, use is made of a quantity of phosphine such that the number of g atoms of phosphorus per g atom of palladium lies in the range of from 0.5 to 1000, preferably from 2 to 100.

It is possible, of course, without departing from the scope of the present invention, to generate "in situ" the catalytic species required for the reaction to take place, by charging a palladium(+2) complex or a palladium(+2) carboxylic acid salt (palladous acetate or palladous propionate) into the reaction medium, together with the appropriate quantity of free phosphine. Therefore, as defined herein, the term "a source of a palladium/phosphine complex" refers to a palladium/phosphine complex either added as such or formed "in situ."

The reaction may be carried out over a wide range of temperatures. In general, a temperature in the range of from 50 to 250° C. is suitable. A temperature of from 80 to 200° C. is preferably used.

The process of the present invention may be carried out at a carbon monoxide pressure equal to atmospheric pressure or at a higher pressure. The pressure of carbon monoxide is preferably from 1 to 150 bars, more preferably less than 150 bars, and most preferably less than 80 bars. Pressures of from 1 to 50 bars are highly suitable.

The molar ratio of carbon monoxide to hydrogen is not critical and may vary within wide limits. Thus, a large excess of either of these reactants may be used. More particularly, the ratio of $CO/H_2$ may vary in a range of from 0.1 to 10.

From a practical standpoint, the process of the present invention is carried out by merely passing a stream of carbon monoxide and hydrogen through an organic solution of the haloarenetricarbonylchromium and the other compounds required for the reaction to take place, or by the action of a pressure of carbon monoxide and hydrogen on said solution, in a stirred, pressure-resistant vessel. When the reaction is completed, the various components of the reaction medium are separated by the usual methods. Depending on the reaction conditions, a greater or lesser proportion of the aromatic aldehyde produced is present in the form of an arenetricarbonylchromium. The reaction medium is then heated to a high temperature under sufficient pressure of carbon monoxide to cause decoordination of chromium and the aromatic aldehyde which may be recovered.

The invention will be described more completely with the aid of the following examples, which should not be considered as limiting the invention. The haloarenetricarbonylchromiums used in the examples were prepared by heating a haloaromatic compound to reflux with hexacarbonylchromium in a mixture of tetrahydrofuran and butyl ether.

EXAMPLE 1

The following were charged into a 100-ml stainless steel autoclave fitted with a heating system and a magnetic stirrer:

1 millimole of chlorobenzenetricarbonylchromium
0.02 millimole of $PdCl_2[P(C_6H_5)_3]_2$
0.1 millimole of triphenylphosphine
20 ml of toluene, and
0.16 ml (1.2 millimole) of triethylamine.

The autoclave was purged with a stream of CO and then closed. Carbon monoxide was then charged in up to a pressure of 15 bars, followed by 15 bars of hydrogen, and then the mixture of reactants was heated to 120° C. with stirring. These conditions were maintained for 5 hours. The autoclave contents were then cooled to 20° C. and degassed.

An aliquot portion of the reaction mass was sampled and used to identify the products formed by means of mass and proton NMR spectrometry. Benzaldehyde was determined by flame ionization gas phase chromatography. It was found that 0.54 millimole of benzaldehyde was formed, representing 54% of the chlorobenzenetricarbonyl originally charged (actual yield).

A further 0.15 millimole of formylarenetricarbonylchromium was determined in the reaction medium, representing 15% of the chlorobenzenetricarbonyl charged. Overall, the benzaldehyde formed represents 69% of the chlorobenzenetricarbonylchromium charged.

EXAMPLE 2

0.7 millimole of chlorobenzenetricarbonylchromium, 0.014 millimole of dichlorobis(triphenylphosphino)palladium, 0.84 millimole of triethylamine, 0.07 millimole of triphenylphosphine and 22.5 g of chlorobenzene were charged into the apparatus of Example 1. The autoclave was purged with a stream of carbon monoxide, closed, and then charged with 1 bar of carbon monoxide, followed by 1 bar of hydrogen. The temperature was raised to 130° C., with stirring. These conditions were maintained for 24 hours and then the reaction mass cooled to 20° C. and the autoclave degassed.

The benzaldehyde formed was determined as in Example 1. The actual yield was 65%.

EXAMPLE 3

The method of Example 2 was employed but at a pressure of 15 bars of CO and 15 bars of hydrogen.

A 52% yield of benzaldehyde was obtained.

EXAMPLES 4 to 7

The conditions of Example 3 were used, with chlorobenzenetricarbonylchromium replaced by various chloroarenecarbonylchromiums. The results shown in the following table were obtained:

| Examples | Substrate | Aldehyde | AY %* |
|---|---|---|---|
| 4 | 1-Chloro-4-methyl-benzenetricarbonyl-chromium | p-Tolualdehyde | 36 |
| 5 | 1-Chloro-4-trifluoro-methylbenzenetricarbonylchromium | 4-Trifluoro-methylbenz-aldehyde | 20 |
| 6 | 1-Chloro-4-methoxy-benzenetricarbonyl-chromium | p-Methoxybenz-aldehyde | 30 |
| 7 | 1-Bromo-4-dimethyl-aminobenzenetricar-bonylchromium | p-Dimethylamino-benzaldehyde | 35 |

*AY stands for actual yield

We claim:

1. A process for the preparation of an aromatic aldehyde by hydrocarbonylation of a chloro- or bromoaromatic compound comprising the step of reacting a mixture of carbon monoxide and hydrogen with chloro- or bromoarenetricarbonyl chromium in the presence of an acceptor for an oxygen-free acid selected from the group consisting of alkaline-earth metal oxides and hydroxides, alkali metal or alkaline-earth metal carbonates or bicarbonates, alkali metal or alkaline-earth metal carboxylates, tertiary amines and tertiary nitrogenous heterocyclic bases and of a source of palladium/phosphine complex catalyst at a termperature of from 50° C. to 250° C. and an absolute pressure of carbon monoxide of from 1 to 150 bars.

2. The process of claim 1, wherein a free phosphine is also present during the reaction.

3. The process of claim 1, wherein an aldehyde of the formula (I):

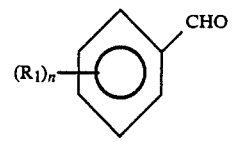

is prepared by hydrocarbonylation of a chloro-or bromoarenetricarbonylchromium compound of the formula (II):

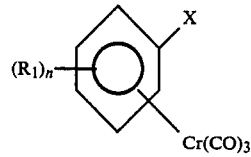

wherein $R_1$ denotes an alkyl radical containing from 1 to 20 carbon atoms, a cycloalkyl radical, an arylalkyl radical, an alkoxy radical containing from 1 to 20 carbon atoms, a fluorine atom, a mono- or polyhalogenated alkyl residue, a formyl group, a carbonyloxyalkyl group, a tertiary amino group, a hydroxyl group, an acyl residue or an acylamine residue;

n denotes an integer from 1 to 3; and

X denotes a chlorine or bromine atom.

4. The process of claim 3, wherein n denotes an integer from 1 to 2.

5. The process of claim 3, wherein in formulae (1) and (II) $R_1$ denotes an alkyl radical containing from 1 to 4 carbon atoms.

6. The process of claim 1, wherein the quantity of acceptor for an oxygen-free acid is at least approximately 1 mole per mole of chloro- or bromoarenetricarbonylchromium.

7. The process of claim 1, wherein the catalyst used is a palladium/phosphine complex selected from the group consisting of the compounds of formulae:

$$Pd(CO)P[(R_2)_3]_3 \qquad (IV)$$

$$Pd_3(CO)_3[P(R_2)_3]_m \qquad (V)$$

$$Pd[P(R_2)_3]_4 \qquad (VI)$$

$$PdZ_2[P(R_2)_3]_2 \qquad (VII)$$

wherein $R_2$ denotes a saturated aliphatic or alicyclic or aromatic hydrocarbon radical containing from 1 to 20 carbon atoms, Z denotes a halogen atom or an acyloxy residue of the formula $R_3$—COO— in which $R_3$ denotes an alkyl, cycloalkyl or arylalkyl radical containing from 1 to 20 carbon atoms, or aryl; and m is 3 or 4.

8. The process of claim 7, wherein in the compound of formulae (IV) to (VII), at least one of the radicals $R_2$ denotes an aryl radical.

9. The process of claim 8, wherein dichlorobis(triphenylphosphino)palladium is used as a catalyst.

10. The process of claim 1, wherein the quantity of catalyst, expressed in gram-atoms of palladium per mole of chloro- or bromoarenetricarbonylchromium, is in the range of from $1 \times 10^{-5}$ to 0.5 gram-atom per mole of chloro- or bromoarenetricarbonylchromium.

11. The process of claim 2, wherein the quantity of free phosphine, expressed in gram-atom of phosphorus per gram-atom of palladium, ranges from 0.5 to 1000.

12. The process of claim 11, wherein the free phosphine is is the same as that present in the phosphine/palladium complex.

13. The process of claim 1, wherein the reaction is carried out in an inert organic solvent.

14. The process of claim 13, wherein the organic solvent used is the tertiary nitrogenous base also employed as said acceptor for an oxyqen-free acid.

15. The process of claim 13, wherein the organic solvent used is selected from the group consisting of a saturated aliphatic hydrocarbon, a saturated alicyclic hydrocarbon, an aromatic hydrocarbon, a halogenated aromatic hydrocarbon, an ether and a lactam.

16. The process of claim 13, wherein the haloaromatic compound from which said chloro- or bromoarenetricarbonylchromium is derived is used as said organic solvent.

17. The process of claim 1, wherein the molar ratio of carbon monoxide to hydrogen is from 0.1 to 10.

18. The process of claim 1, wherein the molar ratio of carbon monoxide to hydrogen is from 0.1 to 10.

* * * * *

UNITED STATES PATENT AND TRADEMARK OFFICE
CERTIFICATE OF CORRECTION

PATENT NO. : 4,720,594
DATED : January 19, 1988
INVENTOR(S) : Jean-Marie Basset et al.

It is certified that error appears in the above-identified patent and that said Letters Patent is hereby corrected as shown below:

Claim 1, column 7, line 61, "termperature" should be --temperature--.

Claim 5, column 8, line 34, "(l)" should be --(I)--.

Claim 14, column 9, line 14, "oxyqen" should be --oxygen--.

Signed and Sealed this

Twenty-sixth Day of July, 1988

Attest:

DONALD J. QUIGG

Attesting Officer

Commissioner of Patents and Trademarks